(12) United States Patent
Davis

(10) Patent No.: US 8,541,470 B2
(45) Date of Patent: Sep. 24, 2013

(54) TOPICAL PHARMACEUTICAL FORMULATION

(75) Inventor: Adrian Francis Davis, Dorking (GB)

(73) Assignee: Futura Medical Developments Limited, Guildford, Surrey (GB)

( * ) Notice: Subject to any disclaimer, the term of this patent is extended or adjusted under 35 U.S.C. 154(b) by 168 days.

(21) Appl. No.: 12/530,960

(22) PCT Filed: Feb. 15, 2008

(86) PCT No.: PCT/GB2008/000540
§ 371 (c)(1),
(2), (4) Date: Dec. 4, 2009

(87) PCT Pub. No.: WO2008/110741
PCT Pub. Date: Sep. 18, 2008

(65) Prior Publication Data
US 2010/0099767 A1    Apr. 22, 2010

(30) Foreign Application Priority Data
Mar. 13, 2007 (GB) .................................. 0704846.5

(51) Int. Cl.
*A61K 31/196* (2006.01)
*A61P 29/00* (2006.01)

(52) U.S. Cl.
USPC ........................................................ 514/567

(58) Field of Classification Search
USPC ........................................................ 514/567
See application file for complete search history.

(56) References Cited

U.S. PATENT DOCUMENTS

2005/0244522 A1    11/2005    Carrara et al. ................ 424/756

FOREIGN PATENT DOCUMENTS

| EP | 0 245 126 A | 11/1987 |
|----|-------------|---------|
| EP | 1 588 697 | 10/2005 |
| WO | WO 01/60336 | 8/2001 |
| WO | WO 2004/017998 | 3/2004 |
| WO | WO 2005/027977 | 3/2005 |

OTHER PUBLICATIONS

Galeotti (Menthol: a natural analgesic compound, Neuroscience letters 322 (2002), pp. 145-148).*
PCT International Search Report and Written Opinion, dated Jan. 13, 2009.
Obata et al. (Int. J. Pharm; 89 (32), 191-198 (1993)) entitled: "*Effect on ethanol on Skin permeation of nonionized and ionized diclofenac*".

* cited by examiner

*Primary Examiner* — San-Ming Hui
*Assistant Examiner* — Kathrien Cruz
(74) *Attorney, Agent, or Firm* — Morgan Lewis Bockius LLP

(57) ABSTRACT

A composition for topical application of an NSAID comprises a solution or suspension of the NSAID in a carrier system comprising a polyhydric alcohol, a glycol ether and an ester of A higher fatty acid, the carrier system being present as a single phase at ambient temperatures. The NSAID may be diclofenac as diclofenac acid. The polyhydric alcohol may be a glycol such as isopropylene glycol and the glycol ether may be a diethylene glycol ether such as diethylene glycol monoethyl ether.

21 Claims, 2 Drawing Sheets

TOPICAL PHARMACEUTICAL FORMULATION

This is a U.S. National Phase Entry of PCT Application No. PCT/GB2008/000540, filed Feb. 15, 2008, with a priority date of Mar. 13, 2007, based upon Application No. GB 0704846.5 filed in Great Britain.

This invention relates to topical pharmaceutical formulations and, in particular, provides a topical formulation for application of a non steroidal anti-inflammatory drug (NSAID) for regional transdermal delivery to underlying tissue for analgesic purposes.

It is already known to provide formulations containing NSAIDs in the form of gels, creams and sprays intended for topical application for regional delivery to underlying tissues, for the relief of pain and inflammation and to restore mobility: However, some NSAIDs exhibit undesirable side effects either on their own or in interaction with other drugs and, for this reason, there is a continuing need to provide a topical formulation which provides an effective amount for therapeutic activity at the regional tissue target below the application site while at the same time preventing general uptake in the systemic circulation. The objective is to provide local efficacy without the potential for systemic adverse consequences such as gastric, hepatic, renal and other effects. The efficacy of known topical formulations does not compare favourably with that of orally-administered compositions which, however, have general uptake in the systemic circulation.

Many NSAID drugs have been formulated for topical-regional delivery including salicylates, indomethacin, piroxicam, ketoprufen, diclofenac and others. Effective topical therapy, whether for local dermal, regional or transdermal therapeutic purposes, requires the achievement of therapeutic drug concentrations at the target site and depends among other things on drug potency and the extent of skin penetration. For topical regional purposes, diclofenac, ketorolac and ketoprofen are preferred; in particular, the efficacy index for diclofenac is greater than that for piroxicam by a factor in the order of $10^3$ demonstrating the importance of correct drug selection. Diclofenac and ketoprofen are particularly preferred on the basis of their more rapid systemic clearance compared with other drugs. Overall, diclofenac is the preferred NSAID for topical regional application. Trials of a 1% diclofenac sodium gel for use in treating ostheoartluitis have demonstrated efficacy and safety, although other diclofenac formulations show efficacy which is inferior to that derived from oral therapy. One currently-available formulation is marketed as "Voltarol Emulgel P", containing 1.16% of diclofenac diethylammonium, equivalent to 1 g of diclofenac sodium per 100 g of gel.

In terms of achieving optimum efficacy following topical application, it is appropriate to consider the rate of metabolism in the skin (where rapid metabolism would reduce the potential for local efficacy) and clearance from the systemic circulation (where slow clearance would tend to result in therapeutic levels building up in plasma), which factors vary considerably between different drugs. It has been found from in vivo human studies that topical application of a 4% diclofenac sodium gel achieves skin concentrations which are 2-3 times higher than a therapeutic oral dose of 15 mg diclofenac taken 3 times daily for 3 days, despite having a plasma concentration lowered by approximately 60 times.

Certain currently-available formulations of diclofenac salts are based on the use of a non-volatile solvent such as propylene glycol in combination with a volatile solvent such as ethanol or isopropanol or mixtures thereof. The purpose of the volatile solvent is to increase solubility and also to lead to volume reduction on evaporation in use and thus an increase in diclofenac concentration in the non-volatile, residual phase. Supersaturation of the diclofenac salts in the residual phase may occur but, in any event; it is the degree of saturation in the residual phase which drives the percutaneous penetration process, since diffusion is more a function of chemical potential rather than absolute diclofenac concentration. By way of example, the saturated solubility of diclofenac acid in polyethylene glycol is 11.18% w/w, whereas in propylene glycol the saturated solubility is only 1.16% w/w. Despite this, there is no significant difference between diclofenac flux from these respective systems and indeed, because the saturated solubility of the sodium salt of diclofenac acid in propylene glycol is approximately 50% w/w, it is very difficult to achieve saturation, more especially supersaturation, unless either extremely high concentrations of the salt are used, or an extremely low percentage of the residual phase solvent is used.

Carrara (US2005/0244522) describes the use of natural (plant derived) skin permeation enhancers in combination with a diethylene glycol ether and, optionally, propylene glycol to deliver a range of drugs including diclofenac diethyl ammonium in cream form. Diclofenac in vitro penetration is approximately twice that of Voltarol gel. Bauer (EP1588697) describes acrylate hydrogels containing an oxyethylene or oxypropylene emulsified lipophilic phase optionally containing propylene glycol and isopropyl myristate to deliver a range of drugs including diclofenac acid and lysine salt in cream form.

Previous studies by Obata et al (Int. J. Pharm; 89 (32), 191-198 (1993)) have taught that diclofenac salts are capable of delivery of more active ingredient transdermally than diclofenac acid, despite having a reduced skin permeability coefficient. This is because ionised forms of diclofenac acid have greater solubility in aqueous solvents and can thus be incorporated in higher concentrations, this compensating to some extent for the reduced skin permeability coefficient of salts. For this reason, all currently-available formulations containing diclofenac for topical application use the salt form. However, with high concentrations of active ingredient, there is a risk of excess drug absorption with resultant local and systemic adverse effects, especially where local skin damage results in higher skin permeability than would otherwise be expected. Diclofenac acid would therefore be regarded as a preferred form for topical application, provided that it could be delivered to the regional tissue target in effective amounts despite its lower solubility compared with ionised forms.

Attempts to use diclofenac acid in water-ethanol and glycerol-propylene glycol mixtures have been made, based on a concentration of diclofenac acid between 2.5 and 5% by weight of the formulation, it having been calculated that such a dose should deliver an effective but essentially non-systemic regional amount assuming a product application rate of 2.5 mg/cm$^2$/hour. However, since the saturated solubility of diclofenac acid is only 5% w/w even in pure ethanol and also since the saturated solubility in propylene glycol is relatively high, at around 1% w/w, it is apparent that only low degrees of saturation are achievable unless low percentages of propylene glycol are used. Although higher alcohols, for example propanol or iso-propanol, may be used as partial or total replacement for ethanol, it has been found that the respective saturated solubilities for diclofenac acid are in the region of 3-4% and thus are less than in ethanol.

It is therefore an object of the present invention to provide a viable topical formulation for the delivery of an NSAID, especially diclofenac acid, in an effective amount to a target site.

In one aspect, the present invention provides a composition for topical application of an NSAID, the composition comprising a solution or suspension of the NSAID as active ingredient in a carrier system comprising a polyhydric alcohol, a glycol ether and an ester of a higher fatty acid, the carrier system being present as a single phase at ambient temperatures.

In compositions according to the present invention, water is essentially absent from the carrier system except in impurity amounts, although the compositions are water-miscible. The presence of water in amounts above impurity levels has been found to have an adverse effect on skin penetration since it militates against a single-phase system. Compositions according to the invention, when applied topically to the skin over an infected or injured target site, become absorbed through the stratum corneum to the underlying tissue to provide a residual phase which continuously releases active ingredients over a period of time to provide a sustained dose to the target site. Compositions according to the invention are preferably in the form of a lotion, cream or gel and include further excipient ingredients as required.

The NSAID which is preferred for use as the active ingredient in compositions according to the invention is diclofenac, due to its cyclo-oxygenase activity in relation to pain and inflammation and because its numerical ratio of skin penetration to potency is superior to most if not all other NSAIDs. Preferably, diclofenac is used as diclofenac acid, it having been found that, in compositions according to the invention, the acid has a significantly higher membrane permeability than salt forms; thus compensating for its relatively low solubility. Other possible NSAIDs for use in the present invention include ketorolac and ketoprofen.

Of the components of the carrier system of compositions according to the invention, the polyhydric alcohol, preferably a glycol, renders the active ingredient soluble in the stratum corneum barrier and also increases the solubility of the ester. The ester, preferably a polar lipid, has the effect of increasing diffusivity or transport rate through the stratum corneum barrier. However, the polyhydric alcohol and ester are immiscible and thus do not form a homogeneous, single-phase carrier system for the active ingredient. The glycol ether is included as a co-solvent and has a polarity between that of the polyhydric alcohol and the ester and is present in an amount at least sufficient to solubilise the other two components and provide a homogeneous, single-phase carrier system.

The polar lipid, as an exemplary sub-class of the esters of a higher fatty acid, may comprise a branched-chain alkyl ester of a $C_{12}$ to $C_{20}$ saturated carboxylic acid such as isopropyl myristate or isopropyl palmitate. The glycol ether, referred to for convenience as a co-solvent with the polyhydric alcohol, is preferably a diethylene glycol ether, for example diethylene glycol monoethyl ether (Transcutol®).

Compositions according to the present invention may have the following amounts of the carrier system ingredients, percentages being given by weight:—

| | |
|---|---|
| polyhydric alcohol | 5-70% |
| glycol ether | 20-60% |
| ester | 2-70% | with the proviso that the carrier system is present as a single phase at ambient temperatures. By "ambient temperatures" is meant room temperature under most climatic conditions, say from 5° C. to 40° C., but including the possibility of temperatures down to 0° C. to allow for refrigerator storage.

The amount of the NSAID in compositions according to the invention may be up to 10% by weight, preferably up to 5% by weight or more preferably up to 2.5% by weight.

As previously stated, the preferred NSAID is diclofenac acid as the free acid.

Within the above concentration ranges for the components of the carrier system, the ratio of polyhydric alcohol to glycol ether is preferably in the range 80:20 to 30:70, more preferably 70:30 to 40:60, with the ester ranging from 2 to 20%, more preferably 3 to 10% by weight. By way of example, one formulation according to the invention contains propylene glycol and Transcutol at a ratio by weigh of 70:30 with isopropyl myristate at 3-3.5% by weight.

Figure 1:
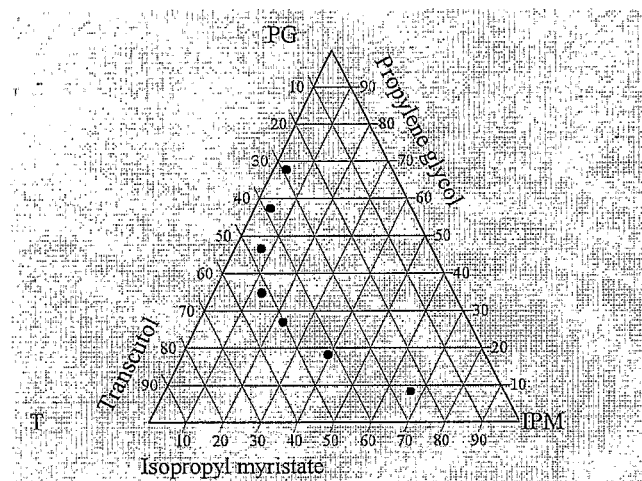
FIG. 1 is a phase diagram of the carrier system comprising propylene glycol, Transcutol and isopropyl myristate.

Referring to FIG. 1, which is a phase diagram showing the effect of addition of a co-solvent (Transcutol) to mixtures of propylene glycol and isopropyl myristate (polar lipid), the phase boundary is represented by the curve joining the points of the single-phase system where the polar lipid is at unit, saturated thermodynamic activity. The area to the left of the phase boundary relates to single-phase systems and, as can be seen on following the phase boundary curve from 70:30 glycol:Transcutol to 10:90 glycol:Transcutol, the polar lipid concentration can be increased while saturation is maintained.

The different carrier systems which from the phase diagram are seen to be possible in terms of enabling inclusion of the polar lipid at saturation amounts have different solubilising powers for diclofenac acid.

Figure 2:
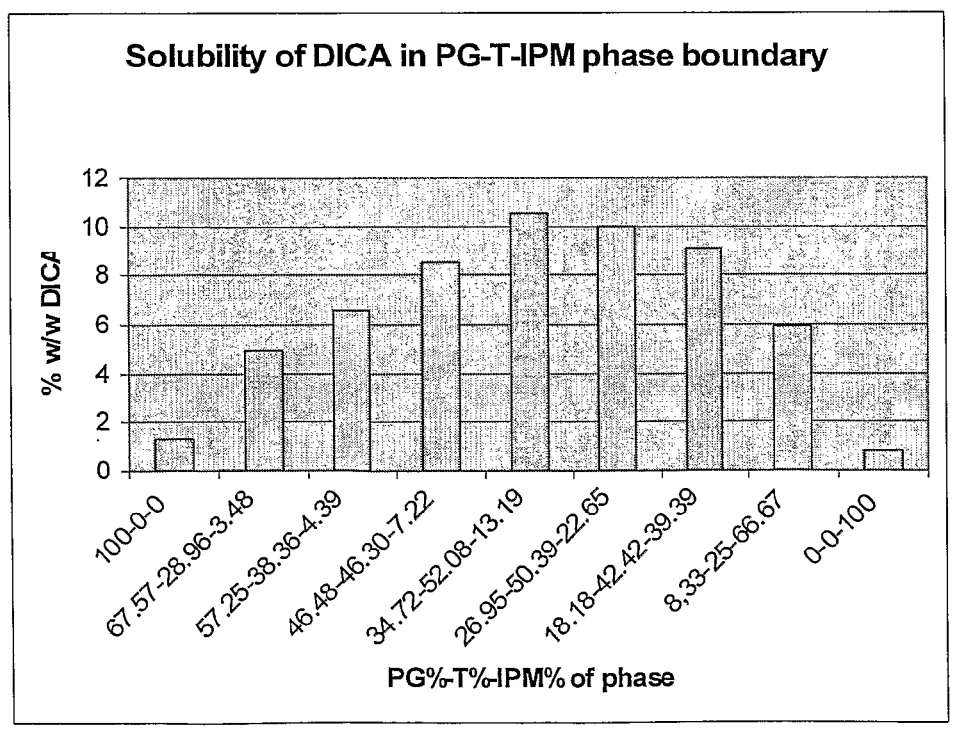
FIG. 2 is a bar graph illustrating the solubility of diclofenac acid in various carrier systems.

The accompanying FIG. 2 is a bar graph showing solubility of diclofenac acid in phase boundary systems as the co-solvent (middle figure of three as wt %) is increased (in glycol-rich systems) and then deceased (in polar lipid-rich systems). Solubility of diclofenac acid is seen to be dependent primarily on the amount of co-solvent, although the ratio of glycol to polar lipid, where co-solvent is present, has a secondary effect on solubility.

In terms of the concentration of diclofenac acid in the composition, it is desirable to provide a dose level sufficient to sustain the percutaneous absorption process and to achieve therapeutic tissue levels at the target site resulting in inhibitory concentrations in the range $IC_{90-99}$. Taking account of steady state plasma levels, diclofenac acid clearance rates and the area over which a topical formulation is typically applied, compositions according to the present invention can be formulated to provide a target in vivo flux of between 5 and 25, preferably 10-20, $\mu g/cm^2/hr$ which, assuming a twice daily (12 hours) dosing regime, requires a concentration of diclofenac acid of around 2.5% by weight, within a broader range of from 1 to 5% by weight.

Optionally, compositions according to the invention also include a volatile solvent which, in conjunction with the other components of the carrier system, solubilizes the active ingredient at saturation levels and evaporates on application to the skin, thus driving the active ingredient to supersaturation in the residual phase, resulting in enhanced flux of active ingredient. Volatile solvents suitable for use in the present invention includes lower alcohols containing up to 5 carbon atoms, for example ethanol, and liquid-phase ketones.

By "liquid phase" in relation to ketones in this specification is meant a ketone having the formula R—C(O)—R which is liquid at ambient temperatures and in which the R groups are the same or different and are alkyl groups optionally substituted by OH, halogen, acetyl (whereby the ketone is acetyl acetone), or other group which, by virtue of its chemical nature or its effect on electron distribution, enhances the solubility properties of the solvent or its rate of evaporation in use. Thus, although higher homologues than acetone, for example, methylethylketone or diethylketone, may be used, acetone is considered to be especially useful because of its ability to undergo keto-enol tautomerism, where the enol form is more stable. Indeed, acetyl acetone, also capable of undergoing keto-enol tautomerism, exists substantially as the enol form.

To enhance stability in a supersaturated residual phase which may have a tendency to instability, it is desirable that the composition also includes an antinucleating agent, to discourage recrystallisation of the drug component, which would lead to lower amounts being available for uptake. Nucleation and recrystallisation are likely to be most problematical where higher degrees of supersaturation are experienced in the residual phase. Antinucleating agents may comprise antinucleant polymers, including cellulose, for example hydroxypropylmethyl cellulose, ethyl cellulose, hydroxypropylmethyl cellulose acetate succinate, and hydroxypropylmethyl cellulose phthalate; pyrrolidones, for example polyvinylpyrrolidone and polyvinylpyrrolidone vinyl acetate copolymer; and acrylates/methacrylates.

Compositions according to the invention may also include sensory signals, for example menthol and eucalyptus oil. Almost immediately after application these agents give a cooling sensation to the skin which is appreciated by users and heralds the onset of pain relief. Other optional ingredients, as known in the art, may be added to compositions according to the invention for formulation purposes depending on the intended mode of application, including thickening or gelling agents, propellants for spray formulations and so on.

Overall, to provide a saturation level of diclofenac acid in the range of approximately 1.0% to 5.0% concentration by weight, and to optimize the glycol and polar lipid component, it is preferred to employ carrier systems on or close to the phase boundary and relatively rich in glycol, that is, those systems which lie in the upper part of the phase diagram of FIG. 1.

In order to predict in vivo rates of human skin penetration, in vitro experiments are generally used, since there is an established correlation between in vitro and in vivo performance. Such systems, as shown in FIG. 1, have been found to provide optimised levels of flux across human skin, and very significant enhancement of flux compared with Voltarol as control, as shown by the results presented in the following Table 1:

TABLE 1

| Formulation | Steady state flux (from t = 6 h-24 h) $\mu g/cm^2/h$ (mean ± SE, n = 6-7) normalized at 2.5% DICA |
|---|---|
| F1, 70:30 | 2.21 ± 0.24 |
| F2, 60:40 | 1.90 ± 0.11 |
| F4, 40:60 | 0.61 ± 0.04 |
| F7, 25:75 | 1.19 ± 0.16 |
| Voltarol | 0.01 ± 0.00 |

It is believed that compositions according to the present invention yield enhanced results for skin penetration due to the factors of high thermodynamic activity of the diclofenac acid as a saturated or supersaturated solution, resulting in increased flux; the ability of the glycol to increase the solubility of the diclofenac acid and the polar lipid in the stratum corneum; and the effect of the polar lipid within the stratum corneum, of increasing diffusivity of diclofenac acid. Since each of these factors is independent of the others, any increase in one of them has a multiplicable effect on the remainder.

Tables 2 gives formulations for the carrier system components only. In formulations containing diclofenac and other excipients the ratio of the three cosolvents is maintained but absolute levels adjusted accordingly.

TABLE 2

| | Formulation - Excipients only | | | | |
|---|---|---|---|---|---|
| | F1: 70-30 | F2: 60-40 | F4: 40-60 | F6: 30-70 | F7: 25-75 |
| Propylene glycol | 67.56 | 57.25 | 34.72 | 18.18 | 8.33 |
| Transcutol | 28.96 | 38.36 | 52.09 | 42.43 | 25.00 |
| IPM | 3.48 | 4.39 | 13.19 | 39.39 | 66.67 |
| Total | 100.00 | 100.00 | 100.00 | 100.00 | 100.00 |

It has been found in experimental in vitro studies that compositions according to the invention give results for epidermal penetration over time periods up to 24 hours which are superior to Voltarol by a factor of up to 100 times or more.

Figure 3:
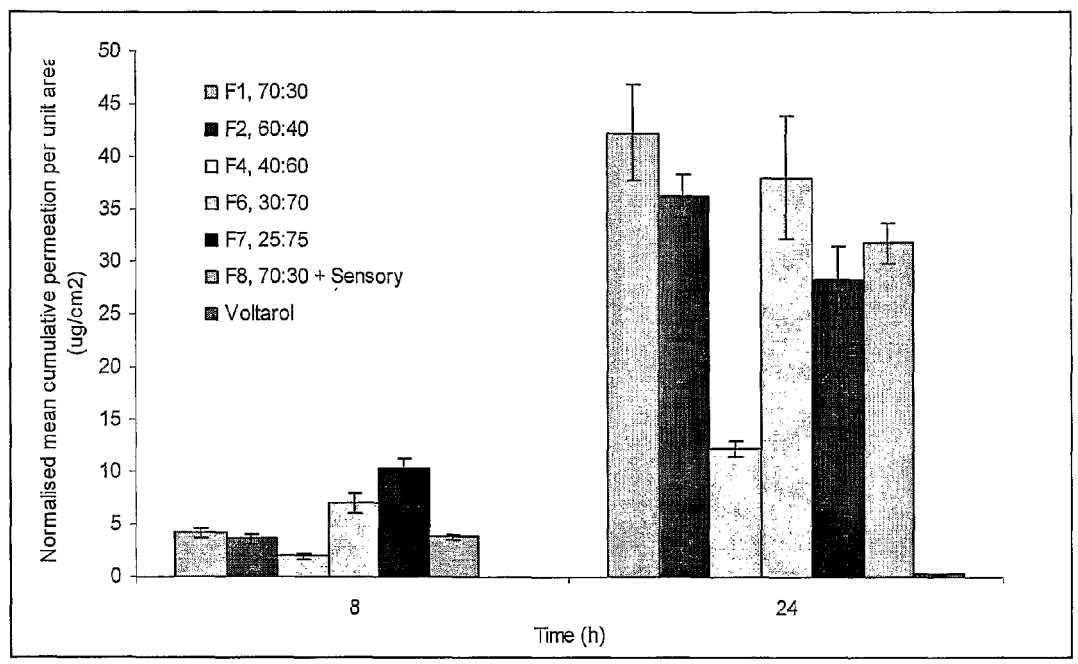
FIG. 3 is a bar graph illustrating predicted skin permeation of diclofenac acid from various carrier systems.

The accompanying FIG. 3 shows predicted mean cumulative penetration of diclofenac per unit area over time (8 hours and 24 hours) from a composition containing 2.5% by weight diclofenac, compared with Voltarol. The data in FIG. 3 was calculated using Equations 1 and 2 as follows:—

$$\text{Adjustment Factor} = \frac{\text{Saturated solubility of each formulation} (\% \text{ w/w})}{\text{Target dose } 2.5\% \text{ (w/w)}} \quad \text{Equation 1}$$

$$\text{Predicted permeation} = \frac{\text{Cumulative amount per unit area } (\mu g/cm^2)}{\text{Adjustment Factor}} \quad \text{Equation 2}$$

A prediction of the relative flux from compositions containing 2.5% (w/w) of diclofenac, are set out in the following Table 3, compared with Voltarol. The formulation F8 is based on F1 with addition of 3% menthol and 1.5% eucalyptus oil.

TABLE 3

| Formulation | Flux (t = 6 h-24 h) μg/cm$^2$/h (mean ± SE, n = 6-7) |
|---|---|
| F1: 70-30 | 2.21 ± 0.24 |
| F2: 60-40 | 1.90 ± 0.11 |
| F4: 40-60 | 0.61 ± 0.04 |
| F6: 30-70 | 1.90 ± 0.16 |
| F7: 25-75 | 1.19 ± 0.16 |
| F8: 70-30 + sensory | 1.64 ± 0.11 |
| Voltarol | 0.01 ± 0.00 |

Figure 4:
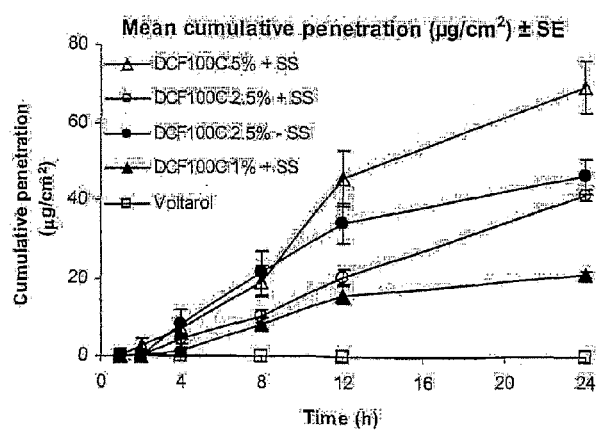
FIG. 4 is a graph showing human skin penetration results for compositions according to the invention compared with Voltarol.

FIG. 4 shows human skin penetration of three concentrations of diclofenac acid in F8, compared to F1 (without sensory) and Voltarol control. All doses show very significantly superior skin penentration to Voltarol control. In these formulations silicone anti-tack and HPC HF (hydroxypropyl cellulose) gelling agent were added as minor excipients. The formulations of these gels are shown in Table 4 below.

TABLE 4

Formulation of F1: (70-30). Aka DCL100C gels

| Formulation | DICA | PG (%) | T (%), actual | IPM (%) | Menthol | Euc | Dimethicone | HPC HF | total |
|---|---|---|---|---|---|---|---|---|---|
| DCL100C 1% + S | 1.0 | 59.42 | 28.52 | 3.57 | 3.0 | 1.5 | 1.5 | 1.5 | 100.01 |
| DCL100C 2.5% + S | 2.50 | 58.44 | 28.05 | 3.51 | 3.0 | 1.5 | 1.5 | 1.5 | 100.0 |
| DCL100C 5.0% + S | 5.0 | 56.82 | 27.27 | 3.41 | 3.0 | 1.5 | 1.5 | 1.5 | 100.0 |
| DCL100C 2.50% − S Gel | 2.50 | 61.36 | 29.46 | 3.68 | — | — | 1.5 | 1.5 | 100.0 |

The invention claimed is:

1. A composition for topical application of an NSAID, the composition comprising
a solution or suspension of the NSAID as active ingredient in a carrier system comprising
a polyhydric alcohol,
a glycol ether and
an ester of a higher fatty acid, wherein the composition is in a single phase at ambient temperatures, wherein water is essentially absent from the carrier system except in impurity amounts, and wherein the composition is not multiple phase.

2. The composition according to claim 1, wherein the NSAID as the active ingredient is diclofenac.

3. The composition according to claim 2, wherein diclofenac is present as diclofenac acid.

4. The composition according to claim 1, wherein the polyhydric alcohol comprises a glycol.

5. The composition according to claim 1, wherein the ester comprises a polar lipid.

6. The composition according to claim 5, wherein the polar lipid comprises a branched-chain alkyl ester of a $C_{12}$ to $C_{20}$ saturated carboxylic acid.

7. The composition according to claim 1, wherein the glycol ether comprises a diethylene glycol ether.

8. The composition according to claim 1 having the following amounts of the carrier system ingredients, percentages being given by weight:

| polyhydric alcohol | 5-70% |
|---|---|
| glycol ether | 20-60% |
| ester | 2-70%. |

9. The composition according to claim 1, wherein the amount of the NSAID is up to 10% by weight.

10. The composition according to claim 1, wherein the ratio of polyhydric alcohol to glycol ether is in the range 80:20 to 30:70 with the ester ranging from 2 to 20% by weight.

11. The composition according to claim 10, wherein the ratio of polyhydric alcohol to glycol ether is in the range 70:30 to 40:60 and the ester is in the range 3 to 10% by weight.

12. The composition according to claim 1, further comprising a volatile solvent.

13. The composition according to claim 12, wherein the volatile solvent comprises a lower alcohol containing up to 5 carbon atoms.

14. The composition according to claim 1, further comprising an antinucleating agent.

15. The composition according to claim 1, further comprising sensory signals.

16. The composition according to claim 4, wherein the glycol is isopropylene glycol.

17. The composition according to claim 7, wherein the diethylene glycol ether is diethylene glycol monoethyl ether.

18. The composition according to claim 9 wherein the amount of the NSAID is up to 5% by weight.

19. The composition according to claim 18 wherein the amount of the NSAID is up to 2.5% by weight.

20. The composition according to claim 13, wherein the volatile solvent is ethanol or a liquid-phase ketone.

21. The composition according to claim 15, wherein the sensory signals comprise menthol, eucalyptus oil or a mixture thereof.

* * * * *